(12) United States Patent
Kwon et al.

(10) Patent No.: US 8,704,004 B2
(45) Date of Patent: Apr. 22, 2014

(54) ETHER-BASED REACTIVE PLASTICIZER FOR PLASTIC BONDED EXPLOSIVES

(71) Applicant: Agency for Defense Development, Daejeon (KR)

(72) Inventors: Young Hwan Kwon, Daegu (KR); Jin Seuk Kim, Daejeon (KR); Bum Jae Lee, Daejeon (KR); In Joo Bae, Daejeon (KR)

(73) Assignee: Agency for Defense Development, Daejeon (KR)

( * ) Notice: Subject to any disclaimer, the term of this patent is extended or adjusted under 35 U.S.C. 154(b) by 0 days.

(21) Appl. No.: 13/762,066

(22) Filed: Feb. 7, 2013

(65) Prior Publication Data

US 2014/0031593 A1    Jan. 30, 2014

(30) Foreign Application Priority Data

Jul. 25, 2012  (KR) .................. 10-2012-0081304

(51) Int. Cl.
*C07C 43/14* (2006.01)
*C07C 205/03* (2006.01)
*C07C 41/09* (2006.01)

(52) U.S. Cl.
USPC ........................................ 568/590; 568/944

(58) Field of Classification Search
USPC ................................... 568/590, 944
See application file for complete search history.

(56) References Cited

U.S. PATENT DOCUMENTS

| | | | |
|---|---|---|---|
| 3,655,836 A | 4/1972 | Dehm et al. | |
| 4,108,926 A | 8/1978 | Arnold et al. | |
| 5,061,330 A | 10/1991 | Reed, Jr. et al. | |
| 5,520,756 A | 5/1996 | Zeigler | |
| 6,736,913 B1 | 5/2004 | Hatch | |
| 7,208,637 B2 * | 4/2007 | Kim et al. | 568/590 |

OTHER PUBLICATIONS

Chemical Propellants & Polymetric Materials, Advance in Research of Energetic Plasticizers, 2003, pp. 20-25.
George Wypych, Handbook of Plasticizers, 2004; pp. 20-23, 66-67.

* cited by examiner

*Primary Examiner* — Brian J Davis
(74) *Attorney, Agent, or Firm* — Harness, Dickey & Pierce, P.L.C.

(57) ABSTRACT

Disclosed is an energetic reactive plasticizer for a plastic bonded explosive (PBX), and specifically an energetic reactive plasticizer for PBX which has high performance and insensitiveness without a plasticizer leak by being bonded with a polymer binder for a plastic bonded explosive.

2 Claims, 4 Drawing Sheets

ETHER-BASED REACTIVE PLASTICIZER FOR PLASTIC BONDED EXPLOSIVES

CROSS-REFERENCE TO RELATED APPLICATION

This application claims the benefit and priority of Korean Patent Application No. 10-2012-0081304, filed Jul. 25, 2012. The entire disclosure of the above application is incorporated herein by reference.

TECHNICAL FIELD

The present invention relates to an energetic reactive plasticizer for a plastic bonded explosive, and specifically to an energetic reactive plasticizer for a plastic bonded explosive which has high performance and insensitiveness without a migration problem of a plasticizer by being bonded with a polymer binder for a plastic bonded explosive.

BACKGROUND ART

Currently, efforts to make energetic materials insensitive have been a significant issue in development of explosives and a propellant. As a part of such efforts, plastic bonded explosives (PBXs) having low sensitivity and improved mechanical properties while maintaining high energy properties have been developed. Such PBX now becomes an elementary component of high-energy explosives, polymeric binders and other additives used in a small amount such as a plasticizer or a stabilizer.

Currently, a polyurethane polymeric binder on the basis of a hydroxyl-terminated polybutadiene (HTPB) has been used as a widely applicable polymeric binder system, together with various additives so as to improve processability, mechanical properties and chemical stability. Although such polymeric binder shows excellent properties in making high-energy materials insensitive, it has been proposed that it generally disadvantageously reduces the energy density of PBX on the whole owing to its low energy potential. In this regard, many studies have been being made to increase the whole energy density through development of energetic binders and plasticizers containing energetic functional groups such as, for example, nitro ($C-NO_2$), nitrate ($O-NO_2$), nitramine ($N-NO_2$), azido ($-N_3$) and difluoroamino ($-NF_2$) and application thereof.

The term "energetic functional groups" as used herein has common and general meaning as used in the field of molecular explosives, i.e, referring to functional groups, when being applied to a molecular explosive or a plasticizer, known to contribute to the increase in the whole energy level of PBX to which the explosive or plasticizer were applied. Nitro ($C-NO_2$), nitrate ($O-NO_2$), nitramine ($N-NO_2$), azido ($-N_3$), difluoroamino ($-NF_2$) or the like as described above may be mentioned. The term "energetic" as used herein means that the whole energy level of a molecular explosive is more increased by any known methods comprising the introduction of such "energetic" functional groups.

However, those polymeric binders and plasticizers which comprise such energetic functional groups have problems such as low heat stability, non-compatibility with explosives and low processability. Therefore, it has been an important rising issue to ultimately achieve both high performance and insensitiveness in explosives. Further, when an energetic plasticizer is applied, an additional problem such as a migration of the energetic plasticizer from PBX occurs over a long period of time. Such migration of an energetic plasticizer involves further additional problems in PBX such as increase in sensitivity to impact and decrease in storage stability and long-term stability owing to deterioration in mechanical properties. Therefore, the realization of an explosive having both high performance and insensitiveness still has been an important matter to be achieved in this field of art.

When a highly energetic polymer which can satisfy both high performance and insensitiveness at the same time is prepared, it is anticipated to obtain a novel energy material which is combined with a molecular explosive and a binder and has an excellent performance and safety.

SUMMARY OF THE INVENTION

The present invention is to provide an energetic reactive plasticizer which can satisfy the high performance and insensitiveness required in the next-generation explosives without a plasticizer migration and thereby preventing various problems accompanied with such migration.

DETAILED DESCRIPTION OF THE INVENTION

PBX is majorly composed of a molecular explosive and a prepolymer and a curing agent for the formation of a binder, and additionally comprises other additives such as a plasticizer on necessary. All the components are introduced, mixed together and then loaded into a container for an explosive, this procedure of which is called a casting process. The prepolymer and the curing agent react in the container to form a binder while solidifying the components in the container.

The 'reactive plasticizer' is a high energy alkyne compound having low viscosity, which can be served as a plasticizer during mixing of PBX and attached to a polymer in a casting or curing process as above. The reactive plasticizer acts as a plasticizer in the preparation of PBX, and a part of or the whole plasticizer is bound into a binder by click reaction by itself in a curing process of the final preparation process.

The present inventors have found that by using a reactive plasticizer in a way of introducing high energy prepolymers in PBX preparation process, it acts as a plasticizer during the casting process, thereby solving the conventional viscosity problem and further it binds to a binder during a curing process, thereby reducing bleeding or migration of a plasticizer, and thus completed the present invention.

In other words, the present invention provides a novel reactive plasticizer having high energy potential by comprising a high energy functional group as well as a functional group which can react with a corresponding energetic prepolymer/a curing agent during a curing process in the preparation of a binder for PBX, thereby being bound to the high energy polymer binder as a side chain thereof.

The energetic reactive plasticizer according to the present invention binds with a side chain of a binder via a click reaction between azide and acetylene groups during the curing process. For such reaction, the energetic reactive plasticizer of the present invention comprises acetylene functional groups and the bond between the energetic functional group and the reactive functional group is an ether bond. In this regard, the novel energetic reactive plasticizer according to the present invention may be classified as an ether-based reactive plasticizer having high energy potential, considering the type of bond characteristically formed in the backbone of the compound is an ether bond.

The ether-based energetic reactive plasticizer is an ether-based compound obtained according to the following reaction scheme 1:

[Reaction scheme 1]

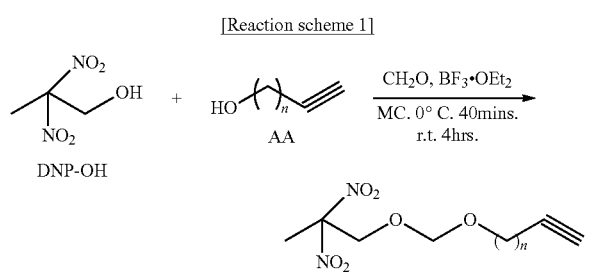

(wherein, n=a natural number selected from 1-10).

As seen from the above reaction scheme 1, the reactive energetic plasticizer containing ether groups in the backbone chain is formed by the acetal formation reaction between 2,2-dinitropropanol (DNP-OH) and an acetylene-containing alcohol (AA).

The acetal formation reaction is carried out by the reaction between aldehyde and an excessive amount of alcohol, under the conventional reaction conditions known in this field of art, so that an energetic reactive plasticizer comprising ether groups in the backbone chain is synthesized by the competitive reaction between DNP-OH and an acetylene-containing alcohol. The acetylene-containing alcohol used in the above reaction includes for example, propargyl alcohol (n=1) and 3-butyn-1-ol (n=2), resulting in 3-((2,2-dinitropropoxy)methoxy)propyne (DNPMPY) or 4-((2,2-dinitropropoxy)methox)-but-1-yne) (DNPMBY), respectively.

EXAMPLES

Preparation Example 1

Synthesis and analysis of 3-((2,2-dinitropropoxy)methoxy)propane (DNPMPY)

An energetic reactive plasticizer, DNPMPY was synthesized by an acetal forming reaction as shown in the following reaction scheme 2.

[Reaction scheme 2]

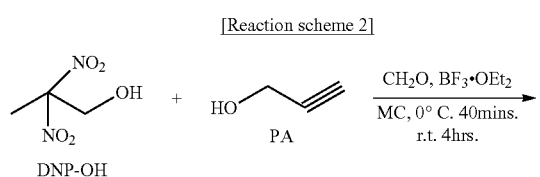

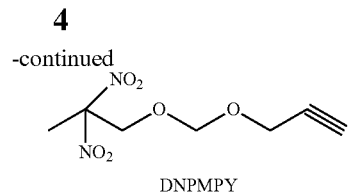

DNPMPY 30 mL methylene chloride (MC), DNP-OH (5 g, 33.56 mmol) and propargyl alcohol (PA) (5.64 g, 100.68 mmol) were placed into a 2-neck flask under nitrogen atmosphere, and then 1,3,5-trioxane (2.21 g, 24.61 mmol, or para-formaldehyde) was further placed with stirring. The mixture was stirred at 0° C. for 10 minutes and then $BF_3 \cdot OEt_2$ (10.48 g. 73.83 mmol) was slowly added dropwise. The reaction temperature was elevated to a room temperature and maintained for further reaction for 3 hours. The reactant was poured into 50 mL distilled water, washed with a $NaHCO_3$ (10%) solution and then further washed twice or more with distilled water. After removing the solvent under reduced pressure, it was further purified by chromatography (eluted by ethylacetate: hexane=1:5), thus obtaining DNPMPY.

The conformation of DNPMPY obtained was identified by the following methods. Firstly, $^1H$ and $^{13}C$ NMR were used to identify the molecular structure, resulting in: $^1H$ NMR ($CDCl_3$, d, ppm): 2.20 (—$CH_3$), 2.45 (≡C—H), 4.20 (—$CH_2$—), 4.30 (—$CH_2$—), 4.75 (—$CH_2$—). $^{13}C$ NMR ($CDCl_3$, d, ppm): 20.0, 55.5, 69.0, 79.0, 94.5, 117.5. The elemental analysis (%) regarding the synthesized DNPMPY was carried out, and the results were as follows: calculated for DNPMPY (%): C, 38.53; H, 4.62; N, 12.84, O, 44.01, measured: C, 38.95; H, 4.25; N, 13.64, O, 43.16.

Figure 1:
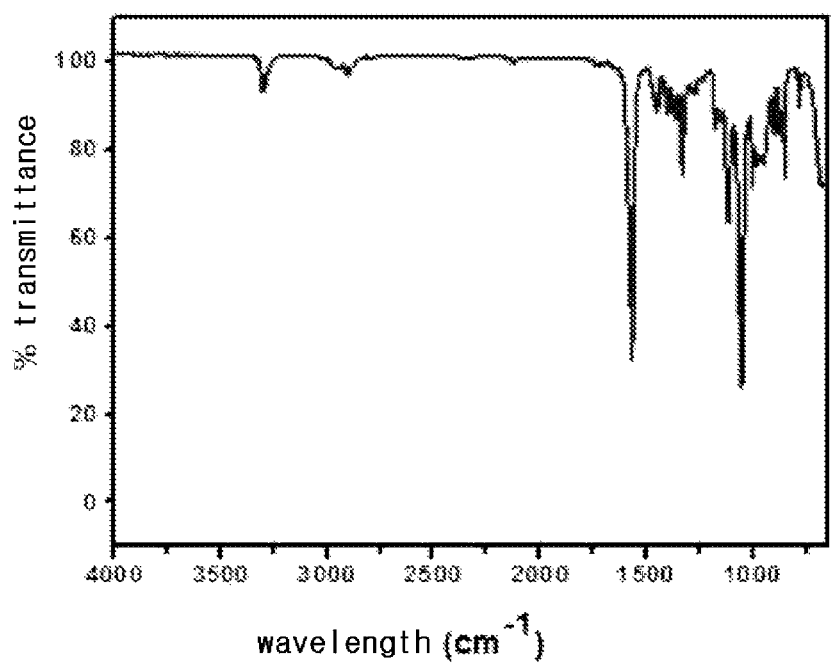
FIG. 1 is a plot showing the FT-IR spectroscopy result of DNPMPY.

As represented in FIG. 1, synthesis of DNPMPY was identified from the absorption peaks of functional groups in FT-IR spectrum results, and the results were as follows: IR ($cm^{-1}$) 3300 (≡C—H), 2930 (aliphatic, C—H), 2300 (—C≡C—), 1590 (—$NO_2$).

Figure 2:
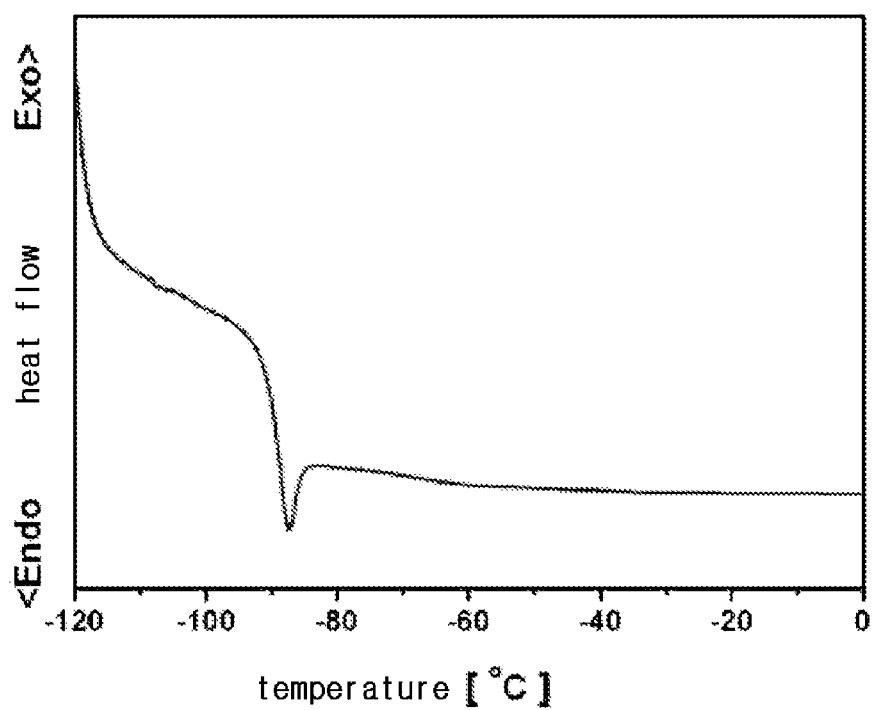
FIG. 2 is a plot showing the DSC result of DNPMPY.

Thermal characteristics of the prepared energetic reactive plasticizer, DNPMPY were measured by differential scanning calorimetry (DSC) and the results were represented in FIG. 2.

According to the DSC results, the glass transition temperature ($T_g$) of the prepared energetic reactive plasticizer, DNPMPY was −89° C., which was about 35° C. lower than Tg of glycidal azide polymer (GAP) plasticizer (−55° C.).

Preparation Example 2

Synthesis and analysis of 4-((2,2-dinitropropoxy)methoxy)-but-1-yne)(DNPMBY)

An energetic reactive plasticizer, DNPMBY was synthesized by an acetal forming reaction as shown in the following reaction scheme 3.

[Reaction scheme 3]

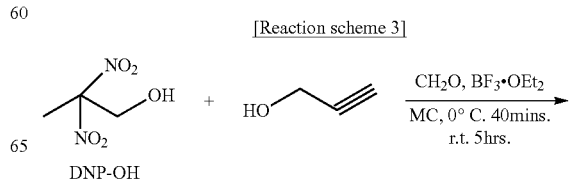

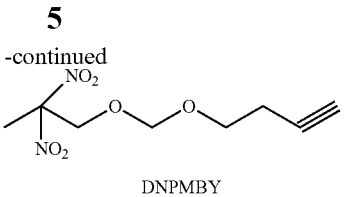

DNPMBY 30 mL methylene chloride (MC), DNP-OH (4 g, 26.85 mmol) and 3-butyne-1-ol (BO) (5.52 g, 80.55 mmol) were placed into a 2-neck flask under nitrogen atmosphere, and then 1,3,5-trioxane (1.61 g, 17.9 mmol, or para-formaldehyde) was further placed with stirring. The mixture was stirred at 0° C. for 10 minutes and then $BF_3 \cdot OEt_2$ (11.44 g, 80.55 mmol) was slowly added dropwise. After stirring at 0° C. for 40 minutes, the reaction temperature was elevated to a room temperature and maintained for further reaction for 5 hours. The reactant was poured into 50 mL distilled water, washed with a $NaHCO_3$ (10%) solution and then further washed twice or more with distilled water. After removing the solvent under reduced pressure, it was further purified by chromatography (eluted by ethylacetate:hexane=1:7 v:v), thus obtaining DNPMBY. The conformation of DNPMBY obtained was identified by the following methods. Firstly, $^1H$ and $^{13}C$ NMR were used to identify the molecular structure, resulting in: $^1H$ NMR ($CDCl_3$, d, ppm): 2.09 (≡C—H), 2.15 (—$CH_3$), 2.44 (—$CH_2$—), 3.61 (—$CH_2$—O—), 4.35 (—O—$CH_2$—O—), 4.68 (—$CH_2$—O—). $^{13}C$ NMR ($CDCl_3$, d, ppm): 20.0, 20.1, 67.1, 69.0, 70.2, 82.1, 96.5, 117.5.

The elemental analysis (%) regarding the synthesized DNPMBY was carried out, and the results were as follows: calculated for DNPMBY (%): C, 41.38; H, 5.21; N, 12.06, O, 41.35, measured: C, 41.60, H, 5.34, N, 12.97, O, 40.09).

Figure 3:
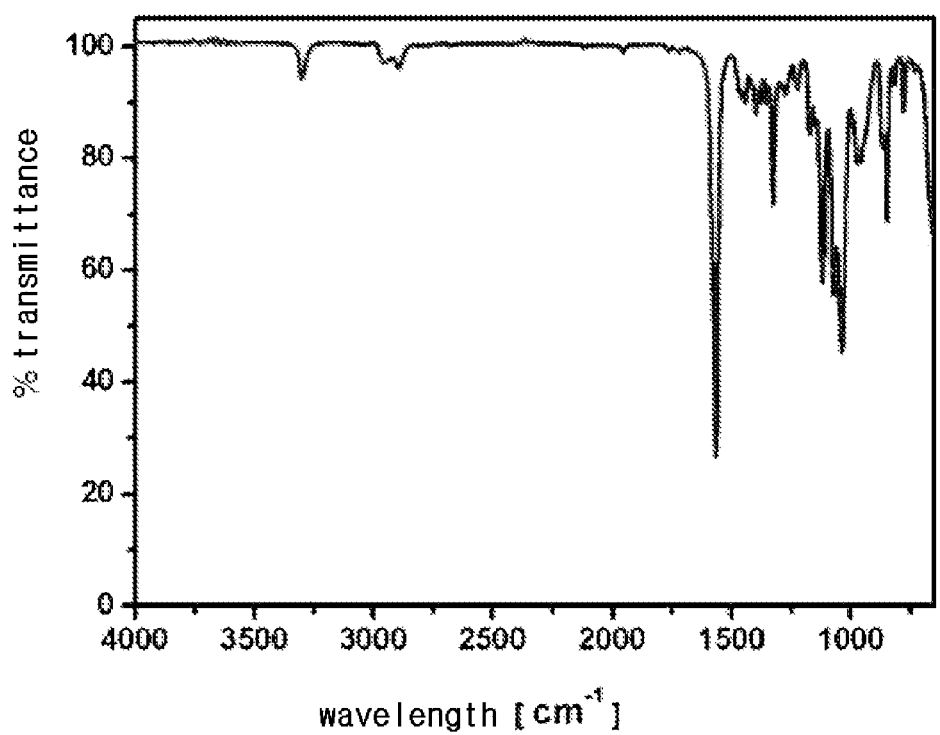
FIG. 3 is a plot showing the FT-IR spectroscopy result of DNPMBY.

As represented in FIG. 3, synthesis of DNPMBY was identified from the absorption peaks of functional groups in FT-IR spectrum results, and the results were as follows: IR ($cm^{-1}$) 3300 (≡C—H), 2930 (aliphatic, C—H), 2300 (—C≡C—), 1590 (—$NO_2$). Plasticization properties of the prepared plasticizer used for PBX preparation were determined by measuring decrease in viscosity of a mixture of said plasticizer and a prepolymer as well as decrease in a glass transition temperature, and the results were shown in the following test example.

Test Example 1

Decrease in Viscosity of a Prepolymer Due to the Plasticizer

Figure 4:
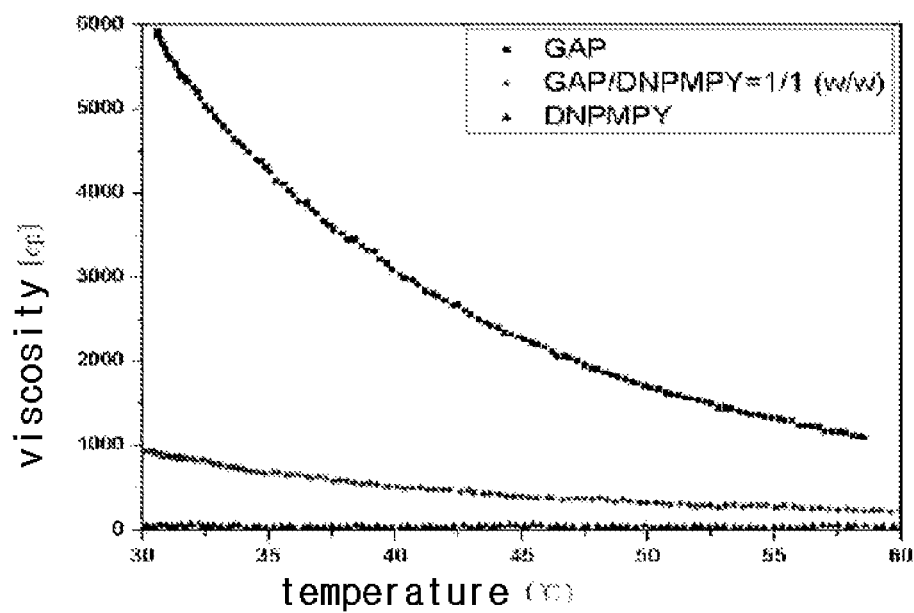
FIG. 4 is a plot showing viscosity changes of GAP polyol prepolymer, prepared DNPMPY and a mixture thereof (1:1 by weight) over temperature, respectively, as measured in the test example 1.

For measuring viscosity, a viscometer, MCR 301 from Anton Paar Physica Co. was used by using a parallel plate having a 1 mm gap (CP25-1-SN9356, diameter=25 mm) at the temperature range of 30-60° C. at a constant shear rate of 1.0 $s^{-1}$ with a temperature elevation rate of 1° C./minutes. After measuring viscosity of GAP polyol prepolymer per se, viscosity of a mixture of DNPMPY plasticizer obtained by the above preparation example 1 and the GAP polyol prepolymer (1:1 w/w) was measured, so as to determine the plasticization properties represented by the decrease in viscosity. The test results obtained from the case where a plasticizer obtained according to the preparation example 1, i.e. DNP-MPY was applied were represented in FIG. 4. As shown in FIG. 4, as compared to viscosity of a GAP polyol prepolymer, viscosity of a mixture of the plasticizer prepared according to the present invention and a GAP polyol prepolymer was significantly lower, over the whole temperature range measured, thereby showing the significant plasticizing effect of the synthesized DNPMPY plasticizer according to the present invention.

The plasticizing effect represented by the decrease in viscosity of a conventionally used energetic plasticizer such as BDNPF/BDNPA; BDNPF/BDNPDF; BDNPF/BDNBF was also shown in the following table 1 for comparison. Viscosity was measured under the same test conditions as described in relation with viscosity measurement of the plasticizer prepared according to the present invention. For reference, viscosity of GAP polyol prepolymer itself was 6,015 cP at 30° C. and 1,035.5 at 60° C., respectively.

TABLE 1

Viscosity of a mixture of GAP polyol prepolymer/plasticizer (1:1 w/w) at 30° C. and 60° C.

| Composition | Viscosity (cP) | |
|---|---|---|
| (1:1 w/w) | 30° C. | 60° C. |
| GAP: DNPMPY | 931 | 227 |
| GAP: BDNPF/BDNPA | 1,441 | 295 |
| GAP: BDNPF/BDNPDF | 1,211 | 197 |
| GAP: BDNPF/BDNBF | 1,351 | 274 |

BDNPF: bis(2,2-dinitropropyl) formal
BDNPA: bis(2,2-dinitropropyl) acetal
BDNPDF: bis(2,2-dinitropropyl) diformal
BDNBF: bis(2,2-dinitrobutyl) formal As seen from Table 1, it can be confirmed that the DNP-MPY plasticizer prepared according to the present invention has an excellent viscosity lowering effect in the GAP polyol prepolymer.

INDUSTRIAL APPLICABILITY

The energetic reactive plasticizer according to the present invention is designed to be present in a form bound to the polymeric binder through covalent bond with the branch of the polymeric backbone of polymeric binder during a curing process, so as to prevent a conventional migration or exudation problem of an energetic plasticizer from the molded plastic PBX, while ensuring the essential physical properties required in an energetic plasticizer used in plastic PBX preparation, such as increased energy density and enhanced processability by lowered viscosity in a blending process.

When the energetic reactive plasticizer according to the present invention is applied to the plastic PBX preparation, the conventional plasticizer migration problem from plastic PBX can be prevented, leading to further advantageous effects such as an improvement in long term storage property of PBX and energy density increase in the whole composition.

What is claimed is:

1. An ether compound represented by the following chemical formula, used for a plasticizer in a preparation of a plastic bonded explosive:

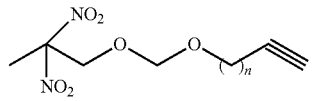

wherein, n=a natural number of 1-10.

2. The ether compound according to claim 1, prepared by the acetal forming reaction between 2,2-dinitropropanol and an alcohol containing an acetylene group.

* * * * *